United States Patent
Dibner et al.

(10) Patent No.: US 6,344,340 B1
(45) Date of Patent: Feb. 5, 2002

(54) VIABILITY ASSAY FOR SPOROCYST-FORMING PROTOZOA

(75) Inventors: Julia Dibner, Chesterfield; Marianne L. Kitchell, Union, both of MO (US); Mary Ann Pfannenstiel, Lincoln, NE (US)

(73) Assignee: Novus International, Inc., St. Louis, MO (US)

( * ) Notice: Subject to any disclaimer, the term of this patent is extended or adjusted under 35 U.S.C. 154(b) by 0 days.

(21) Appl. No.: 09/503,570

(22) Filed: Feb. 14, 2000

Related U.S. Application Data (60) Provisional application No. 60/122,231, filed on Mar. 1, 1999.

(51) Int. Cl.[7] .................... C12Q 1/02; G01N 33/53
(52) U.S. Cl. .................... 435/29; 435/968; 435/242; 435/243
(58) Field of Search .................... 435/29, 968, 242, 435/243

(56) References Cited

U.S. PATENT DOCUMENTS

| | | | |
|---|---|---|---|
| 3,147,186 A | 9/1964 | Edgar et al. | 167/78 |
| 4,438,097 A | 3/1984 | Shirley et al. | 424/88 |
| 4,544,548 A | 10/1985 | Davis et al. | 424/93 |
| 4,666,699 A | 5/1987 | Slifkin | 424/7.1 |
| 4,808,404 A | 2/1989 | Bhogal et al. | 424/88 |
| 5,055,292 A | 10/1991 | McDonald et al. | 424/88 |
| 5,068,104 A | 11/1991 | Bhogal et al. | 424/88 |
| 5,311,841 A | 5/1994 | Thaxton et al. | 604/51 |
| 5,496,700 A | * 3/1996 | Ligler et al. | 435/7.1 |

FOREIGN PATENT DOCUMENTS

| | | | |
|---|---|---|---|
| WO | 94/16725 | 8/1994 | C12N/1/10 |
| WO | 96/40233 | 12/1996 | A61K/39/012 |
| WO | WO-200052195 | * 9/2000 | |

OTHER PUBLICATIONS

Rose, et al., 1980, Vaccination Against Coccidiosis in Chickens, 18th Symp. Br. Soc. Parasitol., pp. 57–74.

Aeschbacher, et al., 1986, *A Rapid Cell Membrane Permeability Test Using Fluorescent Dyes and Flow Cytometry*, vol. 2, pp. 247–255.

Dulski, et al., 1988, The Purification of Sporocysts and Sporozoitess from Eimeria tenella Oocysts Using Percoll Density Gradients, Avian Diseases, vol. 32, pp. 235–239.

Raether, et al., 1991, *Flow cytometric analysis of Eimeria Tanella sporozoite populations exposed to salinomcycin sodium in vitro: a comparative study using light and electron micorscopy and an in vitro sporozoite invasin–inhibition test*, vol. 77, pp. 386–394.

Geysen, et al., 1991, Simultaneous purification of merozoites and schizonts of Eimeria Tenella (Apicomplexa) by percoll flotation and assessment of cell viability with a double fluorescent dye assay, J. Parasitol., vol. 77, pp. 989–993.

Campbell, et al., 1992, Viability of Cryptospordium parvum Oocysts: Correlation of In Vitro Excystation with Inclusion or Exclusion of Fluorogenic Vital Dyes, Applied Environmental Microbiology, vol. 58, pp. 3488–3493.

(List continued on next page.)

*Primary Examiner*—Louise N. Leary
(74) *Attorney, Agent, or Firm*—Senniger, Powers, Leavitt & Roedel (57) ABSTRACT

A method is disclosed for determining the viability of sporocyst-forming protozoa. The method involves treating a sample of protozoa with at least one vital dye and determining the viability of the protozoa in the sample by differential staining. The viability of protozoa in the sample can then be correlated with the viability of protozoa in the population from which the sample was obtained.

24 Claims, 1 Drawing Sheet

OTHER PUBLICATIONS

Davis, et al., 1992 A Rapid, Reliable Method for Evaluating Growth and Viability of Intraerythrocytic Protozan Hemoparasites Using Fluorescence Flow Cytometry, Mem. Inst. Oswaldo Cruz, Rio de Janeiro, vol. 87, pp. 235–239.

Jenkins, et al., 1993, Protective Immunity against Coccidiosis Elicited byRadiation–Attenuated Eimeria maxima Sporozoites that are Incapable of Asexual Development, Avian Dis., vol. 37, pp. 74–82.

Watkins, et al., 1995, The Effect of In Ovo Oocyst of Sporocyst Inoculation on Response to Subsequent Coccidial Challenge, Poultry Science, vol. 74, pp. 1597–1602.

Liegler et al., 1995, Detection and Quantification of Live, Apoptotic, and Necrotic Human Peripheral Lymphocytes by Single–Laser Flow Cytometry, Clin. Diagn. Lab. Immunol., vol. 2, pp. 369–376.

Black, et al., 1996, Comparison of assays for Cryptosporidium parvum oocysts viability after chemical disinfection, FEMS Microbiology Letters, vol. 135, ppl. 187–189.

Brown, et al., 1996, The use of a new viability assay to determine the susceptibility of Cryptosporidium and Eimeria sporozoites to respiratory inhibitors and extremes of pH, FEMS Microbiology Letters, vol. 142, pp. 203–208.

Davey et al., 1996, Flow Cytometry and Cell Sorting of Heterogeneous Microbial Populations: the Importance of Single–Cell Analysis, Microbiological Reviews, vol. 60, pp. 641–696.

Jenkins, et al., 1997, Assessment of a Dye Permeability Assay for Determination of Inactivation Rates of Cryptosporidium parvum Oocysts, Applied and Environmental Microbiology, vol. 63, pp. 3844–3850.

Yang, et al., 1998, In Situ Assessment of Cell Viability, Cell Transplantation, vol. 7, pp. 443–451.

Corominola, et al., 1998, Cryopreservation of Pancreatic Islets Prior to Transplantation: A Comparison between UW Solution and RPMI Culture Medium, Cryobiology, vol. 37, pp. 110–118.

Deng et al. "Cryptospordium Parvum Development in the BS–C–1 Cell Line" Chem. Abstr., vol. 128, No. 22, Abstract 268108v (Jan. 1998) p. 312.

Kaneshiro et al. "Reliability of Calcein Acetoxy Methyl Ester and Ethidium Homodimer or Propidium Iodide for Viability Assessment of Microbes" Chem. Abstr., vol. 119, No. 5, Abstract 44440y (Aug. 1993) p. 460.

Jenkins et al. "X–Irradation of *Eimeria tenella* Oocysts Provides Direct Evidence that Sporozoite Invasion and Early Schizont Development Induce a Protective Immune Response(s)" Infection and Immunity, vol. 59, No. 11 (Nov. 1991) pp. 4042–4048.

Stinear et al. "Detection of a Single Viable *Cryptosporidium parvum* Oocyst in Environmental Water Concentrates by Reverse Transcription–PCR" Applied & Environmental Microbiology, vol. 62, No. 9 (Sep. 1996) pp. 3385–3390.

Vesey et al. "Application of Flow Cytometric Methods for the Routine Detection of Cryptosporidium and Giardia in Water" vol. 16, No. 1 (May 1994) pp. 1–6.

Yokoyama et al. "Fluorochrome Uvitex 2B Stain for Detection of the Microsporidian Causing Beko Disease of Yellowtail and Gold–striped Amberjack Juveniles" Chem. Abstr., vol. 125, No. 17, Abstract 216024h (Oct. 1996) p. 509.

International Search Report for PCT/US00/04574 dated Aug. 2, 2000.

Kaneshiro et al., "Reliability of calcein acetoxy methyl ester and ethidum homodimer or propidium iodide for viability assessment of microbes", *Jour. of Micro. Methods*, 1993, vol. 17, No. 1, pp. 1–16.

* cited by examiner

FIGURE 1

VIABILITY ASSAY FOR SPOROCYST-FORMING PROTOZOA

RELATED APPLICATIONS

This application claims priority to U.S. Provisional Application Ser. No. 60/122,231, filed Mar. 1, 1999 and incorporated herein by reference in its entirety.

BACKGROUND OF THE INVENTION

This invention relates to the determination of live and dead encysted protozoa in a population of protozoa. In particular, the invention relates to the use of vital dyes to determine the viability of sporocysts in a sample and then correlating the extent of staining in the sample with the viability of protozoa in the population from which the sample was obtained.

Coccidiosis is a disease of various animals in which the intestinal mucosa is invaded and damaged by a protozoa of the subclass Coccidia. The economic effects of coccidiosis can be especially severe in the poultry industry where intensive housing of birds favors the spread of the disease. Infection by coccidial protozoa is, for the most part, species specific. Numerous species, however, can infect a single host. For example, there are seven species of Coccidia which infect chickens, six of which are considered to be moderately to severely pathogenic.

The life cycle of the coccidial parasite is complex. For example, protozoa of the genera Eimeria, Isospora, Cystoisospora, or Cryptosporidium typically only require a single host to complete their life cycle, although Cystoisospora may utilize an intermediate host. Under natural conditions, the life cycle begins with the ingestion of sporulated oocysts from the environment. When sporulated oocysts are ingested by a susceptible animal, the wall of the sporulated oocyst is broken in order to release the sporocysts inside. In poultry, the release of the sporocyst is the result of mechanical disruption of the sporulated oocyst in the gizzard. Within the sporocysts are the sporozoites which are the infective stage of the organism. In poultry, the breakdown of the sporocyst coat and release of the sporozoites is accomplished biochemically through the action of chymotrypsin and bile salts in the small intestine. Once released, the sporozoites invade the intestinal mucosa or epithelial cells in other locations. The site of infection is characteristic of the species involved. For example, in the genus Eimeria, *E. tenella* is localized in the ceca; *E. necatrix* is found in the anterior and middle portions of the small intestine; *E. acervulina* and *E. praecox* occur in the upper half of the small intestine; *E. brunetti* occurs in the lower small intestine, rectum, ceca, and cloaca; while *E. mitis* is found in the lower small intestine.

Once inside the host animal's cells, sporozoites develop into multinucleate meronts, also called schizonts. Each nucleus of the meront develops into an infective body called a merozoite which enters new cells and repeats the process. After a variable number of asexual generations, merozoites develop into either microgametocytes or macrogametes. Microgametocytes develop into many microgametes which, in turn, fertilize the macrogametes. A resistant coat then forms around the resulting zygotes. The encysted zygotes are called oocysts and are shed unsporulated in the feces. Infected birds may shed oocysts in the feces for days or weeks. Under proper conditions of temperature and moisture, the oocysts become infective through the process of sporulation. Susceptible birds then ingest the sporulated oocysts through normal pecking activities and the cycle repeats itself. Ingestion of viable, sporulated oocysts is the only natural means of infection.

Infection with Coccidia results in immunity so that the incidence of the disease decreases over time as members of the flock become immune. This self-limiting nature of coccidial infections is widely known in chickens and other poultry. The immunity conferred, however, is species specific such that introduction of another species of Coccidia will result in a new disease outbreak. In addition, infected birds shed considerable numbers of oocysts into the environment so that the introduction of new, previously uninfected birds may result in an outbreak of the disease.

The oocyst wall of Coccidia provides a highly effective barrier for oocyst survival. Oocysts may survive for many weeks outside the host. In the laboratory, intact oocysts are resistant to extremes in pH, detergents, proteolytic, glycolytic, and lipolytic enzymes, mechanical disruption, and chemicals such as sodium hypochlorite and dichromate.

Two methods are currently used to control coccidiosis in poultry. The first involves control by chemotherapy. Numerous drugs are available for the control of coccidiosis in poultry. Because of the number of species which cause the disease, very few drugs are efficacious against all species, although a single drug may be efficacious against several species. In modern broiler chicken production, for example, administration of drugs to control coccidiosis is routine. The expense for preventative medication against coccidiosis in chickens alone has been estimated to exceed $90 million dollars in the United States and $300 million worldwide.

Three programs of drug administration are commonly used in the domestic poultry industry. The simplest is the continuous use of a single drug from day one until slaughter. The shuttle or dual drug program involves the use of two different drugs, one administered in the "starter" ration and a second drug administered in the "grower" ration. In the third method, drugs are rotated in hopes of preventing the development of drug resistant strains.

The development of drug resistance by Coccidia is a serious limitation on the effectiveness of chemotherapy to control the disease. Surveys in the United States, South America and Europe have revealed widespread drug resistance in Coccidia. Since drug resistance is a genetic phenomenon, once established, drug resistance can remain in the population for many years until reduced by natural selection pressure and genetic drift.

The use of drugs in animals used for food production is also coming under increasing scrutiny by the public. Consumers are increasingly concerned with the possibility of drug residues in food. This creates pressure in the poultry industry to reduce the use of drugs to control coccidiosis.

Vaccination of birds against Coccidia is an alternative to chemotherapy. An advantage of vaccination is that it can greatly reduce or eliminate the need to administer anticoccidial drugs, thus reducing costs to poultry producers, preventing the development of drug-resistant strains, and lessening consumer concerns about drug residues.

Numerous methods have been developed to immunize poultry against Coccidia. The successful methods have all been based on the administration of live protozoa, often of an attenuated strain. The most common route of inoculation is oral, although other routes have been used. Edgar, U.S. Pat. No. 3,147,186, teaches vaccination of chickens by oral administration either directly into the mouth or via the feed or water of viable *E. tenella* sporulated oocysts. Davis et al., U.S. Pat. No. 4,544,548, teaches a method of vaccination by continuous administration of low numbers of sporulated oocysts, with or without simultaneous administration of anti-coccidial drugs.

Oral administration of attenuated strains of sporocysts has also been utilized to confer immunity against coccidiosis. Shirley, U.S. Pat. No. 4,438,097; McDonald, U.S. Pat. No. 5,055,292; and Schmatz et al., PCT publication No. WO 94/16725. An alternative to attenuation is disclosed in Jenkins et al., *Avian Dis.*, 37(1):74–82 (1993), which teaches the oral administration of sporozoites that have been treated with gamma radiation to prevent merogonic development.

Parenteral routes of vaccination have included subcutaneous or intraperitoneal injection of excysted sporozoites, Bhogal, U.S. Pat. No. 4,808,404; Bhogal et al., U.S. Pat. No. 5,068,104, and intra ovo injection of either oocysts or sporocysts, Evans et al., PCT publication No. WO 96/40233; Watkins et al., *Poul. Sci.*, 4(10) :1597–602 (1995). Thaxton, U.S. Pat. No. 5,311,841, teaches a method of vaccination against Coccidia by administration of oocysts or sporozoites to newly hatched chicks by yolk sac injection.

One common factor for all methods of vaccinating poultry against coccidiosis, has been the requirement of viable protozoa in order to confer immunity. Use of non-viable protozoa or antigens from protozoa have routinely been unsuccessful in conferring a high level of immunity. Rose and Long, 18$^{th}$ *Symp. Br. Soc. Parasitol.*, pp. 57–74, 1980. Thus, in any vaccination program for coccidiosis, it is critical that viable protozoa be used.

The requirement for living protozoa to confer immunity necessitates that any preparation of protozoa to be used in anti-coccidial vaccines be tested for viability prior to use. In addition, the availability of a rapid, accurate viability test would be useful in screening potential anti-coccidial drugs.

The traditional method of determining the viability of coccidial protozoa has been to administer the organisms to susceptible hosts and wait to see if clinical symptoms develop. Although gross pathology provides a means to evaluate infection, this method is costly, both in terms of animals used and the time to complete the assay. For example, in chickens, it takes 4–7 days after infection for clinical signs of the disease to manifest themselves.

An alternative method to assess viability is the in vitro infection of cells. For example, Raether et al., *Parasitol. Res.* 77(5):386–94 (1991), used the ability of *E. tenella* sporozoites to invade primary chick-kidney cells to assess the effectiveness of salinomycin sodium. Although more economical in terms of animal use, viability assays based on invasion of in vitro cell cultures require days before results can be obtained. In addition, such assays are more qualitative rather than quantitative, since they cannot assay the viability of individual protozoa. What is needed, therefore, is an assay that can rapidly and accurately assess the viability of individual protozoa within a sample.

One method which has been used to assess cell viability in general is the use of vital dyes. Vital dyes are dyes which are able to differentiate between living (vital) and dead (non-vital) cells on the basis of differential staining. One common class of vital dyes relies on membrane integrity to assess viability. Typically with these dyes, viable cells with intact membranes exclude the dye, while cells whose membrane integrity has broken down and so are dead or dying are stained. While there is not an exact equivalence between the presence of an intact cell membrane and the ability of the cell to maintain its existence, it is common in the art to consider cells whose membrane has become irreparably disrupted as dead.

Originally, non-flourescent dyes such a Trypan Blue were used to assess viability. However, due to their greater sensitivity and compatibility with flow cytometers, fluorescent dyes are now commonly used to assess viability based on membrane integrity. Commonly used fluorescent dyes which are excluded from intact cells are polar heterocyclic compounds such as propidium iodide, ethidium bromide and ethidium homodimer.

Viability tests based on differential staining have been applied to a number of cell types and organisms. The use of vital stains and flow cytometry to assess viability of bacteria has been reviewed by Davey and Kell, *Microbiol. Rev.*, 60(4):641 (1996). Differential staining has also been used to assess the viability of a number of cell types including thymocytes (Aeschbacher et al., *Cell Biol. Toxicol.* 2(2):247–55 (1986)), cartilage and corneas (Yang et al., *Cell Transplant.* 7(5):443–51 (1998)), pancreatic islet cells (Corominola et al., *Cryobiology* 37(2):110–18 (1998)), and lymphocytes (Liegler et al., *Clin. Diagn. Lab. Immunol.* 2(3):369–76 (1995)).

The use of vital dyes to assess the viability of Eimeriina protozoa has been more limited. Vital dyes have been used to assess the viability of excysted stages of Eimeria. Raether et al., *Parasitol. Res.* 77:386–94 (1991), used a combination of propidium iodide and fluorescein diacetate to determine the viability of *E. tenella* sporozoites after exposure to salinomycin sodium, an anti-coccidial drug. Brown et al., *FEMS Microbiol. Lett.*, 142(2–3)203–08 (1996) describes a method for assessing the viability of *E. tenella* sporozoites using acridine orange and bis-benzimide. Geysen et al., *J. Parasitol.*, 77(6):989–993 (1991), used a combination of ethidium bromide and acridine orange to assess the viability of *E. tenella* merozoites and schizonts isolated from the intestinal mucosa of infected chickens. Davis et al., *Mem. Inst. Oswaldo Cruz*, 87(Suppl. III):235–239(1992) used the vital dye hydroethidine to measure the viability of the intraerythrocytic form of another member of the class Sporozoea, *Babesia bovis*. The use of vital dyes has apparently found only limited use in determining the viability of encysted protozoa of the Sporozoea class, no doubt due to resistance of the cyst or outer coating to dye penetration.

A notable exception to this is members of the genus Cryptosporidia. A combination of DAPI (4'-6-diamindino-2-phenylindole) and PI (propidium iodide) has been used by several authors as a means to determine the viability of Cryptosporidia oocysts with varying success. Jenkins et al., *Appl. Environ. Microbiol.*, 63(10):3844–50 (1997) and Campbell et al., *Appl. Environ. Microbiol.*, 58(11):3488–93 (1992) reported a strong correlation between viability estimates based on vital staining and in vitro excystation. Jenkins et al., also reported that Cryptosporidia oocysts classified as viable were able to cause infection, but no direct correlation between infectivity and viability as determined by vital staining was made. The accuracy of viability tests in Cryptosporidia based on differential staining has been questioned. Black et al., *FEMS Microbiol. Lett.*, 135(2–3): 187–89 (1996) reported that both DAPI/PI and in vitro excystation assays overestimate infectivity. The success of vital staining of Cryptosporidia species as opposed to other Eimeriina may be due to difference in the life cycle. Unlike other Eimeriina, Cryptosporidia do not form sporocysts. Instead, the sporozoites form in the oocysts. Regardless of the reason why, there have been no reports of successful application of vital dyes to encysted stages of the genus Eimeria.

The present invention provides a rapid, reliable means to assess viability of protozoa in vaccine preparations prior to either distribution or administration. In addition, the present invention may be used in assessing the sensitivity of protozoa to anti-coccidial drugs, both in terms of new drug development and in terms of choosing appropriate anti-coccidial drugs for administration to animals with clinical coccidial infections. Further, the invention may be used to evaluate the effectiveness of agents for use in disinfecting equipment and environments contaminated by coccidial protozoa.

SUMMARY

Among the aspects of the invention, therefore, is a process for determining the viability of sporocyst-forming protozoa. In this process, a sample of sporocysts is obtained from a starting population of protozoa. The starting population can be either a naturally occurring population or one maintained in the laboratory. If the population contains primarily oocysts or sporulated oocysts, the formation of sporocysts can be induced by well established methods. The sporocysts in the sample are treated with at least one vital dye to yield a detectable signal. Staining is then determined using any means suitable for detecting the stained protozoa. By correlation, the viability of the protozoa in the original population can be estimated based on the extent of staining of the protozoa in the sample.

Another aspect of the invention is a method for evaluating the effectiveness of a composition against a sporocyst-forming protozoa. In this method, a first sample containing sporocysts is prepared from a population of sporocyst-forming protozoa and treated with at least one vital dye. The treated sample is then examined for staining and the extent of staining correlated with the viability of the protozoa in the population. The population is then exposed to the composition to be tested, after which a second sample containing sporocysts is obtained. The second sample is also stained with at least one vital dye and the extent of staining examined. The extent of staining in the second sample is correlated with the viability of the protozoa in the population. Thus, by comparing the viability of protozoa in the two samples, the effectiveness of the composition can be determined.

Yet another aspect of the invention is a method for evaluating a means for storing or maintaining sporocyst-forming protozoa. The method comprises, preparing a first sample of sporocysts from a population of sporocyst-forming protozoa and treating the sample with at least one vital dye. The sample is then examined for staining and the extent of staining correlated with the viability of protozoa in the population. The population of protozoa is then stored using the method to be tested and at least on additional sample of sporocysts prepared. The additional sample is treated with at least vital dye and examined for the extent of staining. The extent of staining is then correlated with the viability of the population after storage. The viability of the population before and after storage is then compared to evaluate the storage method.

Still another aspect of the invention is a method for evaluating a management practice for controlling protozoa. The method comprises preparing a first sample of sporocysts obtained from the environment to be managed and treating the sample with at least one vital dye. The extent of staining is then examined and correlated with the viability of protozoa in the environment. The management practice to be evaluated is then implemented. After implementation of the management practice, at least one additional sample of sporocysts from the environment is prepared. The sample is treated with at least one vital dye and examined for the extent of staining. The extent of staining is then correlated with the viability of the protozoa in the environment after implementation of the management practice. By comparing the viability of protozoa in the environment before and after implementation of the management practice, the effectiveness of the practice in controlling protozoa in the environment managed can be assessed.

Yet another aspect of the invention is to assess the viability and hence the infectivity of protozoa found in the environment. The disclosed invention is also useful for assessing the sensitivity of protozoa to anti-protozoal drugs, both in terms of new drug development and in choosing the most effective therapeutic agent for treating animals with protozoal infections. In addition, the invention can be used to evaluate the effectiveness of agents for use in disinfecting equipment and environments contaminated by coccidial protozoa.

BRIEF DESCRIPTION OF THE DRAWINGS

These and other features, aspects, and advantages of the present invention will become better understood with regard to the following description, appended claims and accompanying figures where:

DEFINITIONS

"Oocyst" means the dormant life-cycle stage of a coccidial protozoan having a tough outer coat. As formed, the oocyst is not capable of infection and may also be referred to as an "unsporulated oocyst." Oocysts are found in the intestine of animals following release from infected cells and are eliminated in the excreta.

"Sporulated oocyst" means an oocyst which has undergone maturation naturally or through artificial manipulation such that the sporulated oocyst is capable of infecting a susceptible host. During maturation, a multiplicity of sporocysts, each with its own outer shell or case, develops within the oocyst creating a "cyst within a cyst." For example, in E. tenella, a sporulated oocyst contains four sporocysts, each with their own outer shell or case.

"Sporocyst" means a life-cycle stage of a coccidial protozoan having an outer coat or case containing a multiplicity of sporozoites which are the ultimate infective agent of the protozoan. In the instance of E. tenella, each sporocyst contains two sporozoites.

"Sporocyst-forming protozoa" means protozoa which have as part of their life cycle, at minimum, a non-infective oocyst stage that is shed by infected animals, a sporulated oocyst stage, and a sporocyst stage.

"Encysted protozoa", "encysted oocyst" and "encysted sporocyst" all refer to organisms which are within a cyst or have their own outer coat or shell.

"Excysted protozoa" and "excysted sporozoite" both refer to an organism in which the outer shell or coat has been removed either naturally or through artificial means.

"Vital dye" or "vital stain" means a stain or dye useful for the determination of whether a cell is alive or dead based on differential staining.

"Management practice" means any action undertaken to aid in the husbandry of animals.

As used herein, the term "animal" includes human beings.

PBS means phosphate buffered saline.
TDA means taurodeoxycholic acid.
PI means propidium iodide.
DAPI means 4'-6-diamidino-2-phenylindole.

DETAILED DESCRIPTION

The following detailed description is provided to aid those skilled in the art in practicing the present invention. Even so, this detailed description should not be construed to unduly limit the present invention as modifications and variation in the embodiments discussed herein can be made by those of ordinary skill in the art without departing from the spirit or scope of the present inventive discovery.

All publications, patents, patent applications and other references cited in this application are herein incorporated by reference in their entirety as if each individual publication, patent, patent application or other reference were specifically and individually indicated to be incorporated by reference.

Protozoa cause a number of diseases in man and animals. For example, coccidiosis is a disease of the intestinal tract caused by members of the class Sprorozoea. Coccidiosis can cause major economic losses to animal producers. Members of the genus Eimeria have been reported to cause coccidiosis in cattle, sheep, goats, chickens, turkeys, ducks, geese, reptiles and fish. Members of the genus Isospora cause the disease in pigs, foxes and reptiles. Members of the genus Cryptosporidium have been found to cause coccidiosis in cattle, sheep, goats, pigs, dogs and cats. Coccidiosis in dogs and cats is also caused by members of the genus Cystoisospora. In addition, members of the genera Wenyonella and Tyzzeria cause coccidiosis in ducks.

Surprisingly, it has been discovered that sporocysts are especially well suited for use in viability assays of sporocyst-forming protozoa. It has been discovered that sporocysts, unlike oocysts, are permeable to vital dyes allowing rapid and reliable assessment of viability by a variety of methods. In addition, sporocysts are easier to maintain in vitro than excysted stages, such as the sporozoite, previously used with vital dyes. Furthermore, unlike with later stages, it has been discovered that the viability of sporocysts in a sample is predictive of the viability of the population of oocysts from which the sporocysts were obtained.

In accordance with the present invention, therefore, a method is provided for the determination of the viability of a population of sporocyst-forming protozoa. Thus, the present invention is applicable to any sporocyst-forming protozoa of the class Sporozoea, particularly of the subclass Coccidia and more particularly of the order Eucoccidiida and more particularly still of the suborder Eimeriina. The present invention is particularly applicable to sporocyst-forming protozoa of the genera Cystoisospora, Eimeria, Isospora, Neospora, Sarcocystis, Toxoplasma, Tyzzeria and Wenyonella. In this method, a sample of the population is prepared. If the population is primarily in the sporocyst stage, a sample of the population is simply stained as described herein. If the population is primarily in the oocyst stage, the population can be induced to undergo sporulation by well-known methods for management of the environment or a sample from the population can be induced to undergo sporulation using well-known laboratory methods. If the population or sample is primarily at the sporulated oocyst stage, sporocysts can be readily obtained by methods well known in the art, for example, mechanical disruption with glass beads.

Source of oocysts

Oocysts may be obtained from feces or tissue of infected animals; contaminated feed or water; soil; pen litter or bedding; or a variety of other sources. The exact procedures used will vary with the material from which the oocysts are obtained and will be apparent to those skilled in the art. In one embodiment of the present invention, oocysts are obtained from excreta.

Isolation of oocysts

Various methods for the isolation of oocysts from excreta are known in the art and the method used will only be briefly described herein. The initial step is separation of the oocysts from extraneous material. Excreta is mixed with a minimum of 2 volumes (w/v) of saturated aqueous NaCl to form a slurry. If necessary, the slurry can be processed in a mixer or blender until a homogenous consistency is achieved. The slurry is centrifuged at about 800×g for 10 minutes at 4° C. The supernatant is collected by pouring through a double layer of 24×24 weave cheese cloth. The filtered supernatant is diluted with two volumes of potable water and centrifuged at about 1600×g for 10 minutes at 4° C. The pelleted oocysts are washed with water and pelleted by centrifugation as described an additional three times. The oocysts are then washed three times in 2.5% potassium dichromate using the same procedure used for the water washes. After the final wash, the oocysts can be stored in 2.5% potassium dichromate at 4° C. or transferred to a container for sporulation.

Alternatively, sequential filtration can be used to isolate oocysts based on size. If filtration is used, the oocysts are washed with water and 2.5% potassium dichromate as previously described.

Sporulation

If the protozoa obtained are at the oocyst stage, it is possible to induce sporulation. Various methods to induce sporulation are known to those skilled in the art. For example, sporulation can be accomplished by placing oocysts in a solution of 2.5% potassium dichromate in a container and placing a cotton or foam rubber plug in the opening. The container is agitated on an orbital shaker at 250 rpm and 28–30° C. for 48–72 hours. Alternatively, the solution containing the oocysts can be constantly agitated while air is bubbled through the solution at about 25 to 75 cubic feet per hour. During the sporulation process, samples are withdrawn at regular intervals and tested for sporulation by microscopic examination of the oocysts to determine if they contain sporocysts.

Alternatively, if the sample of protozoa is to be obtained from the environment, for example floor litter, the litter can be managed to provide the proper conditions of moisture and temperature to cause natural sporulation.

Following sporulation, sporulated oocysts are collected by filtration, centrifugation or other acceptable concentration procedures known to those skilled in the art. For example, sporulated oocysts can be concentrated by centrifugation at about 1600×g for 10 minutes at 4° C. and the supernatant discarded. After concentration, sporulated oocysts may be disinfected by suspension in 5.25% sodium hypochlorite for 10 minutes at 4° C. Following disinfection, the sporulated oocysts are removed from the sodium hypochlorite by centrifugation at 1600×g for 10 minutes at 4° C. or other acceptable means. The sporulated oocysts are then washed four to six times with sterile water. After washing, the sporulated oocysts can be stored in 2.5% potassium dichromate, phosphate buffered saline (PBS) containing 30 μg/ml gentamicin or other acceptable disinfectants.

Sporocyst isolation

Methods for isolation of sporocysts are well known to those skilled in the art and will only be briefly described herein. Sporulated oocysts are diluted to a concentration of about $2 \times 10^6$/ml in PBS. One ml of the $2 \times 10^6$/ml suspension of sporulated oocysts is added to 1.5 ml microfuge tubes containing 125 µl of 0.5 mm glass beads. The tubes containing the sporulated oocysts and the glass beads are vortexed at high speed for five minutes and then chilled on ice.

Following vortexing, the supernatant is removed and saved. The glass beads are then washed with PBS and the supernatant saved and combined with the supernatant obtained after vortexing. The supernatant is then centrifuged at about 9020×g for about two to three minutes and the supernatant discarded. The pellet is resuspended in 0.2 ml of PBS. The concentration of sporocysts per ml is then determined by using a hemacytometer or other method of determining cell number.

Stock staining solutions

A stock solution of ethidium bromide is made by adding 100 µl of 10 mg/ml ethidium bromide solution (Gibco BRL No. to 15585-011) to 1.9 ml of double distilled water for a final concentration of 0.5 mg/ml. The stock solution is then stored at approximately 5° C. in the dark until used. A stock solution of 4% TDA is made by addition of sufficient PBS to 0.4 g of taurodeoxycholic acid (Sigma Chemical Co., No. T0875) to make 10 ml. The 4% TDA solution is divided into 0.5 ml aliquots and stored at approximately −20° C. The 4% TDA stock is thawed shortly before use.

Staining

Sporocysts are stained by treatment with a sufficient quantity of at least one vital stain to produce a detectable signal. Any dye or combination of dyes capable of distinguishing between vital (live) and non-vital (dead) cells can be used. In one embodiment, dyes that measure viability on the basis of membrane integrity can be used. Especially useful are nucleic acid staining dyes, such as nucleic acid intercalating dyes. One example, is heterocyclic dyes that are excluded by cells with intact membranes such as the phenanthridinium dyes propidium iodide, ethidium bromide, ethidium monoazide and ethidium bromide homodimer. Another example of a dye that can be used to assess viability based on membrane integrity is calcfluor white (CFW), the disodium salt of 4,4'-bis(4-anilino-bis-diethyl amino-s-triazin-2-ylamino)-2,2'-stilbene disulphonic acid. Viability can also be determined using dyes that measure intracellular enzymatic activity such as carboxy fluorescein diacetate or calcien-AM. Indicators of membrane energization can likewise be used to determine viability. Examples of dyes which provide a measure of membrane energization are rhodamine 123, carbocyanine dyes and dyes of the oxonol family. Other stains suitable for determination of cell viability will be readily apparent to those skilled in the art.

Optionally, a combination of stains can be used. For example, a combination of vital stains can be used so that both live and dead protozoa are stained. The live and dead protozoa are then differentiated on the basis of, for example, color or emission wavelength. An example of such a combination is propidium iodide and carboxy fluorescein diacetate. Another approach is to combine a vital stain with a dye which stains all protozoa regardless of viability to aid, for example, in counting the number of protozoa present. An example of such a combination would be DAPI (4'-6-diamidino-2-phenylindole) and propidium iodide. Other possible combinations of stains will be readily apparent to those skilled in the art.

In one embodiment, protozoa are stained with ethidium bromide. Factors affecting staining conditions include, but are not limited to, such things as the stain used, the detection method employed, the species of sporocyst stained, temperature, the staining solution, and other factors known in the art. Optimal staining conditions can readily be determined by one skilled in the art without undue experimentation. For example, the concentration of ethidium bromide can range up to about 100 µg/ml. When detection is by fluorescence microscopy, the concentration of ethidium bromide is preferably between about 5 µg/ml and 75 µg/ml, more preferably between about 10 µg/ml and 50 µg/ml and more preferably still about 20 µg/ml. When detection is by flow cytometry, the concentration of ethidium bromide is preferably less than 25 µg/ml, more preferably between about 1 µg/ml and about 15 µg/ml, even more preferably between about 2 µg/ml and about 10 µg/ml, more preferably still between about 3 µg/ml and about 7 µg/ml, and most preferably about 5 µg/ml. Likewise, staining temperature can range from about 4° C. to 43° C. It will be appreciated by those skilled in the art that the staining time will vary with the temperature and concentration of stain used, but that staining times can vary from approximately 1 minute to 12 hours. Staining solutions will vary with the stain used. In the present invention, the staining solution preferably contains taurodeoxycholic acid, although other bile salts could be substituted. The concentration of taurodeoxycholic acid can vary from about 0.4% to 10% and preferably is about 4%. Without being limited by theory, taurodeoxycholic acid is thought to increase the permeability of the sporocyst coat without destroying the micropyle cap. Thus, any non-toxic material which increases the permeability of the sporocyst coat without destroying the micropyle cap could be utilized. In another embodiment, sporocysts are stained for approximately 10 minutes at 41° C. in a solution containing between about 5 and 20 µg/ml ethidium bromide and about 4% taurodeoxycholic acid.

Counting

Once stained, it is necessary to count the number of stained and unstained sporocysts in the sample. Any method capable of detecting the presence of a dye in stained protozoa can be used, and many such methods will be apparent to those skilled in the art. For example, and without limitation, when a fluorescent dye is used, a known number of stained sporocysts can be placed in multi-well plates and the amount of fluorescence determined using a fluorescence plate scanner. The number of stained (dead) sporocysts can be determined by constructing a standard curve using known numbers of stained, dead sporocysts. In like manner, the number of stained sporocysts can be determined by fluorometry or fluorescence spectrophotometry.

In one embodiment of the invention, the number of stained and unstained sporocysts is determined using a fluorescence microscope. Sporocysts, for example, can be placed in a hemacytometer slide or wells of a multi-well plate and the total number of sporocysts and the number of stained sporocysts determined. Alternatively, the images obtained through the fluorescence microscope can be captured by image processing software. The software can then be used to, for example, record the location of each sporocyst in the field and then record if that sporocyst fluoresces to calculate the percentage of dead sporocysts in the sample. In yet another alternative, the image analysis system can be combined with a computer controlled microscope stage so that the computer moves the stage to search the slide containing the sample and based on predetermined parameters locates and counts the sporocysts. The process is then repeated under conditions in which only fluorescing cells are counted. The results are then used to calculate the percentage of fluorescing and so dead sporocysts. Since the sum of the percent fluorescing (dead) and non-fluorescing (live) sporocysts is assumed to equal 100%, once the percent dead sporocysts is determined, the percent live sporocysts in the sample can be calculated by subtraction. As shown in Example 3, by back calculation, the results obtained can be used to determine the percent dead in the original sample of sporulated oocysts.

In another embodiment, the number of stained and unstained sporocysts is determined by use of a flow cytometer. The exact data settings used to differentiate live and dead protozoa will vary with factors such as the flow cytometer used, the dye(s) used and the species of protozoa to be analyzed and can be readily determined by those skilled in the art without undue experimentation. Data parameters can be set to differentiate live and dead protozoa on the basis of multiple determinants. For example, when multiple stains are used, the cytometer can be set to acquire data on multiple fluorescence parameters as well as size and density. The data acquired can then be combined to differentiate between live and dead protozoa on the basis of different colors of fluorescence and eliminate interference due to debris or organisms that differ in size from the protozoa of interest.

In a preferred embodiment, the electronic gating of the flow cytometer is set so that only intact sporocysts of the species of protozoa of interest are counted. Data parameters for fluorescence intensity are set using unstained controls such that approximately 95% of the unstained sporocysts are below the threshold to be marked as a stained sporocyst and are recorded as an unstained event, for example, marked M1. The remaining stained sporocysts whose fluorescence intensity exceeds the M1 threshold are marked as stained sporocysts (stained event), for example M2, such that the total of M1 and M2 equals the total number of sporocysts counted. By construction of a single-parameter histogram, the percentage of stained and unstained sporocysts can be determined. Alternatively, the fluorescence threshold to mark an event can be set such that approximately 95% of all stained sporocysts exceed the set threshold, while all sporocysts whose fluorescence intensities are below the threshold are marked as unstained. If the flow cytometer is so equipped, sporocysts can be sorted based on their fluorescence intensity.

The following examples are intended to provide illustrations of the application of the present invention. The following examples are not intended to completely define or otherwise limit the scope of the invention.

EXAMPLES

Example 1

Determination of Sporocyst Viability by Fluorescence Microscopy

Approximately 40,000 sporocysts obtained as previously described were added to each of three 1.5 ml microfuge tubes and an amount of the 4% TDA (taurodexoycholic acid) stock was solution added to make 100 µl. Four µl of the 0.5 mg/ml stock solution of ethidium bromide was then added. The tubes were then incubated in a 41° C. water bath for approximately 10 minutes. Immediately after the incubation period, the tubes were placed on ice and allowed to cool.

Excess ethidium bromide was removed by washing with phosphate buffered saline (PBS). Washing was accomplished by adding the staining solution containing the sporocysts to the upper chamber of a 0.2 µm cellulose acetate spin filter, e.g. Lida series 8000, containing 600 µl of PBS. The spin filter was then centrifuged at about 1023×g for two minutes and the solution at the bottom of the tube discarded. An additional 700 µl of PBS was added to the top of the spin tube and the process repeated. The sporocysts remaining in the top chamber were resuspended in 200 µl PBS by gentle vortexing and placed in the wells of a 96 well plate.

After washing, the number of stained sporocysts was determined. The contents of each tube were transferred to a well of a 96 well plate so that the number of wells containing stained samples corresponded to the number of polystyrene tubes. A fluorescence microscope equipped with a Zeiss 450–490 FT 510 LP 520 filter set was used to count the total number of sporocysts and the number of stained sporocysts. The sporocysts were first examined at 400× magnification under fluorescent illumination and the number of fluorescing sporocysts in a field determined. The same field was then viewed under bright field illumination and the total number of sporocysts in the field determined. A minimum of 50 sporocysts were counted. The results of three replicates were averaged to determine the percent viable and non-viable sporocysts in the sample.

Example 2

Determination of Sporocyst Viability by Flow Cytometry

Sporocysts were stained and washed as in Example 1 except that the amount of ethidium bromide dye used was 1 µl of the 0.5 mg/ml ethidium bromide stock solution per 100 µl of sporocyst sample. An unstained (negative) control and a heat killed (50–55° C., 30 minutes), stained (positive) control were included in each assay.

A Becton Dickinson FACScan flow cytometer with Cell Quest software was used for determination of stained and unstained sporocysts. The instruction manual for the FAC-Scan flow cytometer is herein incorporated by reference. Other flow cytometers can be used in practicing the invention and alternative cytometers will be readily apparent to those skilled in the art.

Approximately 5000 sporocysts were counted per sample. The electronic gating of the flow cytometer was set so that only intact *E. tenella* sporocysts would be counted. The excitation wavelength was set at 488 nm. Data parameters for fluorescence intensity were set using the unstained and heat killed controls so that approximately 90–99% of unstained sporocysts were below the fluorescence intensity threshold and so were marked as M1, an unstained event (unstained sporocyst) while approximately 90–99% of the heat killed sporocysts exceed the fluorescence intensity threshold and were marked M2, a stained event (stained sporocyst).

After the gates for counted events and the M1 and M2 energy levels were set, the three stained replicate samples were analyzed. Following analysis, a single parameter histogram was constructed and the percentage of stained and unstained sporocysts calculated. In one embodiment using ethidium bromide, the percentage of fluorescent sporocysts (M2, % gated) represented the percentage of sporocysts which were dead (non-vital). Since the total number of events equals 100%, the percentage of sporocysts which did not fluoresce (M1, % gated) represented the percentage of live (vital) sporocysts in the sample. The average of the three stained samples was used to determine the viability of the sporocyst preparation.

Example 3

Relationship Between Viability of Siorocysts and Slorulated Oocysts

*E. tenella* sporocysts were collected from two lots of sporulated oocysts designated Control 1 and Control 2. A sample of Control 2 was killed by heating to 50° C. for 30 minutes (dead oocysts). Sporocysts were isolated from sporulated oocysts as previously described. Sporocysts were then stained as described in Example 1. Staining was used to assess viability of sporocysts from control oocysts, dead oocysts and a 50/50 mixture of dead and control oocysts. The results are summarized in Table 1.

Sporocysts were recovered from control and heat treated oocysts at the same rate indicating that dead sporocysts were not preferentially lost or retained during purification. With the control oocysts, 16–20% of the sporocysts stained, indicating that they were dead, while 98% of the sporocysts from the heat treated oocysts stained. When equal mixtures of sporocysts from dead and control oocysts were mixed, the expected percentage of dead sporocysts was obtained within 10%.

TABLE 1

Vital staining of *E. tenella* sporocysts with ethidium bromide

| Sporocyst Source | % Sporocysts Recovered | % Dead (stained) |
|---|---|---|
| Control 1 | 37 | 16[a] |
| Control 2 | 27 | 20 |
| Dead | 24 | 98[a] |
| Control 1/Control 2 (50/50 mix) | — | 19 |
| Dead/Control 1 (50/50 mix) | — | 45 |
| Dead/Control 2 (50/50 mix) | — | 47 |

[a]Average of two separate experiments

Example 4

Assay Accuracy with Mixed Populations of Sporocysts

In order to assess if viability tests conducted on sporocysts could accurately determine the viability of a population of mixed live and dead sporulated oocysts, populations of untreated (control) and heat killed (dead) oocysts were mixed prior to sporocyst isolation. Sporulated oocysts were killed by heating to 50° C. for 30 minutes. Sporocysts were isolated from control oocysts, dead oocysts and a mixture of control and dead oocysts as described in Example 3. Viability of the sporocysts isolated was determined by the observation under a fluorescence microscope after staining as described in Example 1 except that oocysts from lot TPZ-MUS980206 were stained for 5 minutes instead of 10 minutes. The results are summarized in Tables 2 and 3.

Table 2 shows that recovery rates were similar for cocysts, heat-treated dead oocysts and 50/50 mixes of control and dead oocysts. The results using heat-killed sporocysts indicate that the recovery rate of sporocysts is not influenced by the viability of the sporulated oocyst from which they are obtained. Table 3 shows the results of the viability assessments based on staining with ethidium bromide. The actual percent of sporocysts staining dead was similar to the percentage predicted on the basis of live and dead oocysts in the sample from which the sporocysts were obtained. Thus, the percentage of dead sporocysts as determined by ethidium bromide staining can be used to determine the viability of the oocysts from which the sporocysts were obtained.

TABLE 2

Recovery of sporocysts from control and heat killed oocysts.

| Oocyst Lot # | Treatment | % Recovery |
|---|---|---|
| 03 Dec 97 | Control | 32 |
| 03 Dec 97 | 50° C. | 25 |
| 03 Dec 97 | 50/50 mix | 26 |
| TPZMSU980206 | Control | 30 |
| TPZMSU980206 | 50° C. | 31 |
| TPZMSU980206 | 50/50 mix | 28 |

TABLE 3

Fluorescence of sporocysts purified from control and heat killed oocysts.

| Oocyst Lot # | Treatment | % Predicted[a] | % Fluorescent |
|---|---|---|---|
| 03 Dec 97 | Control | Unknown | 11 |
| 03 Dec 97 | 50° C. | 100 | 95 |
| 03 Dec 97 | 50/50 mix | 53 | 46 |
| TPZMSU980206 | Control | Unknown | 9 |
| TPZMSU980206 | 50° C. | 100 | 90 |
| TPZMSU980206 | 50/50 mix | 50 | 50 |

[a]Predicted value for 50/50 mix is the average of the values obtained for the corresponding Control and 50° C. samples.

Example 5

Assay Linearity

Figure 1:
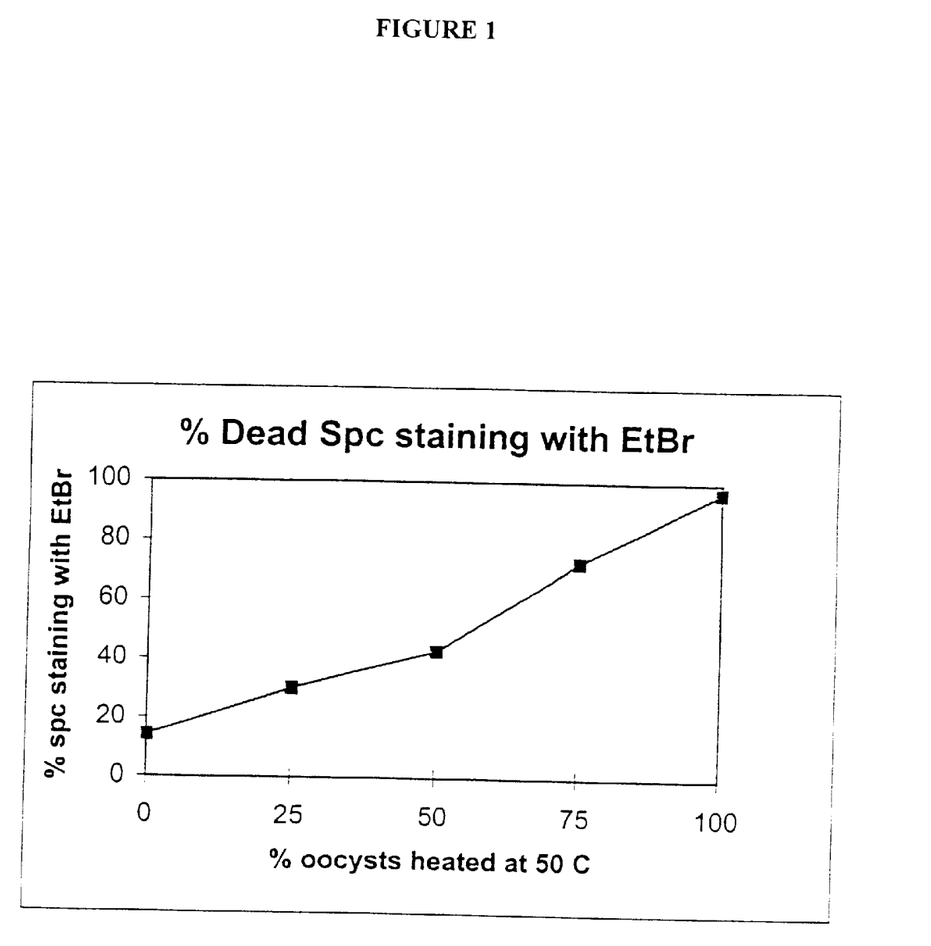
FIG. 1 shows the correlation between percentage of viable protozoa in the sample based on staining versus the predicted percentage of viable protozoa in the sample based on the mixture of untreated and heat killed protozoa used to make the sample.

In order to determine if ethidium bromide staining is able to accurately assess viability in populations of sporocysts that vary substantially in the percent of sporocysts that are viable, various proportions of sporocysts from control and heat killed oocysts were mixed and the predicted and measured percentage of dead sporocysts compared. Sporocysts were stained as described in Example 1 and the number of stained sporocysts determined with a fluorescence microscope. The results, which are presented in FIG. 1, showed a high correlation (correlation coefficient of 0.998) between the percent of dead sporocysts predicted and the percent actually determined.

Example 6

Assay Stability

To determine if the staining was stable over time, sporocysts were stained and assayed as in Example 2 and then stored in the dark for 24 hours at 40° C. The sporocysts where then re-analyzed and the results compared. The results are summarized in Table 4. The change in percent of sporocysts showing fluorescence after 24 hours varied from −2.1 to +2.3. Thus, results of the assay are stable for at least 24 hours.

TABLE 4

Flow cytometric analysis of ethidium bromide stained sporocyst samples immediately after and 24 hours after staining.

| | % Staining (dead) | | |
|---|---|---|---|
| Sample # | Initial Value | 24 hr Value | Difference |
| 3 | 4.7 | 4.2 | −0.5 |
| 21 | 32.6 | 30.5 | −2.1 |
| 22 | 43.5 | 43.8 | +0.3 |

TABLE 4-continued

Flow cytometric analysis of ethidium bromide stained sporocyst samples immediately after and 24 hours after staining.

| Sample # | % Staining (dead) | | |
|---|---|---|---|
| | Initial Value | 24 hr Value | Difference |
| 23 | 10.9 | 11.8 | +0.9 |
| 25 | 91.4 | 90.4 | −1.0 |
| 26 | 98.6 | 98.1 | −0.5 |
| 28 | 88.4 | 90.7 | +2.3 |

Example 7

Relationship Between Staining and Infectivity

Experiments were conducted to determine the relationship between viability as determined by ethidium bromide staining and viability as determined by the ability to infect baby hamster kidney cells in vitro. The use of in vitro cell cultures to determine the infectivity of coccidial protozoa is well known in the art. The baby hamster kidney cells used, line BHK12A, are a clonal cell line derived from BHK21 cells (ATCC CCL10). Methods for development of cell lines from single cells (clonal cell lines) are well known to those skilled in the art. BHK12A cells were cultured in 96 well tissue culture plates to 50% confluence in OptiMem® medium (Life Technologies, 1998 Cat. No. 31985) containing 2% fetal calf serum in an atmosphere of 5% $CO_2$, at 41° C. Other culture media suitable for baby hamster kidney cells, such as Dulbecco's Modified Eagle's Medium (DMEM) may also be used.

Sporocysts were obtained from a population of sporulated oocysts as described previously. A portion of the sporocysts obtained served as untreated controls. The remaining sporocysts were then stained and sorted into stained and unstained populations using a Becton Dickinson FACScan as in Example 2. Alternative, suitable cell sorters will be apparent to those skilled in the art. Sporozoites were then isolated from unsorted control sporocysts; sorted, stained sporocysts (dead); and sorted, unstained sporocysts (live); using the method of Dulski and Turner, *Avian Diseases*, 32(2):235–239 (1988), herein incorporated by reference.

To measure infectivity, culture medium was removed from the BHK12A cells and the cells washed twice with PBS to remove any residual serum. The medium was then replaced with 200 $\mu l$ of serum-free medium and 1000 to 9000 sporozoites from control, stained, or unstained sporocysts were added to each well. After two hours, the medium was supplemented with fetal calf serum (1% final concentration) and the incubation continued for 48 to 60 hours at 41° C. in an atmosphere of 5% $CO_2$ in air. Infectivity was measured as the number of merozoite foci or mature schizonts in two diameters under 400×magnification. The results are shown in Table 5.

No merozoites or schizonts were observed in the wells inoculated with sporozoites obtained from stained (dead) sporocysts. Merozoites were observed in the wells inoculated with sporozoites from both unstained and control sporocysts. The infectivity observed was greater with sporozoites obtained from unstained, sorted sporocysts, than sporozoites from unsorted controls. Thus, there is a positive relationship between viability as determined by vital staining and infectivity as determined by invasion of baby hamster cells.

TABLE 5

Infectivity of sporozoites obtained unsorted control and stained and unstained, sorted sporocysts.

| Sporozoite Source | Infectivity |
|---|---|
| Control sporocysts (not stained or sorted) | 6 |
| Sorted sporocysts-stained fraction (dead) | 0 |
| Sorted sporocysts-unstained fraction (live) | 16 |

In light of the detailed description of the invention and the examples presented above, it can be appreciated that the several aspects of the invention are achieved.

It is to be understood that the present invention has been described in detail by way of illustration and example in order to acquaint others skilled in the art with the invention, its principles, and its practical application. Particular formulations and processes of the present invention are not limited to the descriptions of the specific embodiments presented, but rather the descriptions and examples should be viewed in terms of the claims that follow and their equivalents. While some of the examples and descriptions above include some conclusions about the way the invention may function, the inventors do not intend to be bound by those conclusions and functions, but put them forth only as possible explanations.

It is to be further understood that the specific embodiments of the present invention as set forth are not intended as being exhaustive or limiting of the invention, and that many alternatives, modifications, and variations will be apparent to those of ordinary skill in the art in light of the foregoing examples and detailed description. Accordingly, this invention is intended to embrace all such alternatives, modifications, and variations that fall within the spirit and scope of the following claims.

What is claimed is:

1. A method for determining the viability of a population of sporocyst-forming protozoa comprising:

(a) preparing a sample from the population, the sample containing sporocysts of the sporocyst-forming protozoa, (b) treating the sample with at least one vital dye, (c) examining the treated sample for staining, and (d) correlating the extent of staining of the treated sample with the viability of the sporocyst-forming protozoa in the population.

2. The method of claim 1, wherein staining is examined by microscopy.

3. The method of claim 2, wherein said microscopy is fluorescence microscopy.

4. The method of claim 2, wherein said microscopy further comprises using a computer-assisted image analysis system.

5. The method of claim 1, wherein staining is examined by flow cytometry.

6. The method of claim 1, wherein said at least one vital dye is a fluorescent dye.

7. The method of claim 1, wherein said at least one vital dye is a nucleic acid staining dye.

8. The method of claim 6, wherein said vital dye is an ethidium derivative.

9. The method of claim 8, wherein said vital dye is ethidium bromide.

10. The method of claim 6, wherein said vital dye is a propidium derivative.

11. The method of claim 10, wherein said vital dye is propidium iodide.

12. The method of claim 9, wherein the concentration of ethidium bromide is greater than 0 µg/ml but less than about 100 µg/ml.

13. The method of claim 9, wherein the concentration of ethidium bromide is between about 1 µg/ml and about 40 µg/ml.

14. A method for determining the viability of a population of sporocyst-forming protozoa comprising:
  (a) preparing a sample of the population, the sample containing sporocysts of the sporocyst-forming protozoa;
  (b) treating the sample with ethidium bromide, at a concentration of between about 10 µg/ml and about 50 µg/ml;
  (c) determining the number of viable and non-viable sporocysts in the sample by fluorescence microscopy; and
  (d) correlating the number of viable and non-viable sporocyst-forming protozoa in the treated sample to the number of viable and non-viable sporocyst-forming protozoa in the population.

15. The method of claim 14, wherein the concentration of ethidium bromide is 20 µg/ml.

16. A method for estimating the viability of a population of sporocyst-forming protozoa comprising:
  (a) providing a sample of the population, the sample containing sporocysts of the sporocyst-forming protozoa;
  (b) treating the sample with ethidium bromide at a concentration of between about 2 µg/ml and about 10 µg/ml;
  (c) determining the number of viable and non-viable sporocysts in the sample by flow cytometry; and
  (d) correlating the number of viable and non-viable sporocyst-forming protozoa in the treated sample to the number of viable and non-viable sporocyst-forming protozoa in the population.

17. The method of claim 16, wherein the concentration of ethidium bromide is 5 µg/ml.

18. The method of claim 1, wherein said method is used to estimate the viability of sporocyst-forming protozoa in a composition.

19. The method of claim 18, wherein said composition is a vaccine.

20. The method of claim 1, wherein said steps (a) to (d) are carried out a first time and then a second time to evaluate the effectiveness of a composition against a sporocyst-forming protozoa and wherein said method further comprises contacting the sporocyst-forming protozoa with the composition between said first and second times.

21. The method of claim 1, wherein said steps (a) to (d) are carried out a first time and then a second time to evaluate a method for storing a sporocyst-forming protozoa and wherein said method further comprises storing the sporocyst-forming protozoa for a period between said first and second times.

22. The method of claim 1, wherein said steps (a) to (d) are carried out a first time and then a second time to evaluate a management practice for controlling sporocyst-forming protozoa in an environment and wherein said method further comprises subjecting the protozoa to the management practice between said first and second times.

23. The method of claim 1, wherein said sporocysts are obtained from sporulated oocysts.

24. The method of claim 23, wherein said sporulated oocysts are obtained by treating oocysts to undergo sporulation.

* * * * *